United States Patent
Yeh et al.

(10) Patent No.: US 8,148,519 B2
(45) Date of Patent: Apr. 3, 2012

(54) PORPHYRIN-BASED PHOTOSENSITIZER DYES FOR DYE-SENSITIZED SOLAR CELLS

(75) Inventors: Chen-Yu Yeh, Tainan (TW); Eric Wei-Guang Diau, Hsinchu (TW); Cheng-Wei Lee, Changhua (TW); Hsueh-Pei Lu, Taipei (TW); Chi-Ming Lan, Taoyuan (TW)

(73) Assignees: National Chiao Tung University, Hsinchu (TW); National Chung Hsing University, Taichung (TW)

( * ) Notice: Subject to any disclaimer, the term of this patent is extended or adjusted under 35 U.S.C. 154(b) by 99 days.

(21) Appl. No.: 12/485,811

(22) Filed: Jun. 16, 2009

(65) Prior Publication Data

US 2010/0125136 A1 May 20, 2010

(30) Foreign Application Priority Data

Nov. 17, 2008 (TW) .................................. 97144426

(51) Int. Cl.
*C09D 11/00* (2006.01)
*C07B 47/00* (2006.01)
*C07D 487/22* (2006.01)

(52) U.S. Cl. .................................... 540/145; 106/31.27
(58) Field of Classification Search .................. 540/145, 540/140; 106/31.27
See application file for complete search history.

(56) References Cited

OTHER PUBLICATIONS

Hayashi et al., Chemistry Letters (2008), 37(8), pp. 846-847.*
Kang et al., Bull. Korean Chem. Soc., 2007, vol. 28, No. 1 pp. 33-40.*
Campbell et al., "Porphyrins as light harvesters in the dye-sensitised $TiO_2$ solar cell", Jun. 2004, Coordination Chemistry Reviews 248, p. 1363-1379, Elsevier B.V., www.sciencedirect.com.
Campbell et al., "Highly Efficient Porphyrin Sensitizers for Dye-Sensitized Solar Cells", Jul. 2007, pp. 11760-11762, J. Phys. Chem. C, vol. 111, No. 32.
Luo et al., "Sequential Energy and Electron Transfer in an Artificial Reaction Center: Formation of a Long-Lived Charge-Separate State", Feb. 2000, pp. 6535-6551, J. Am. Chem. Soc., vol. 122, No. 28.
Tomé et al., "Synthesis and Photophysical Studies of New Porphyrin-Phthalocyanine Dyads with Hindered Rotation", 2006, Wiley-VCH Verlag GmbH & Co. KGaA, Weinheim, pp. 257-267, Eur. J. Org. Chem.
Ka and Lee, "Optimizing the synthesis of 5, 10-disubstituted tripyrromethanes", Apr. 2000, pp. 4609-4613, Elsevier Science Ltd.
Grätzel, "Conversion of sunlight to electric power by nanocrystalline dye-sensitized solar cells", Feb. 2004, pp. 3-14, Journal of Photochemistry and Photobiology A: Chemistry 164, www.elsevier.com/locate/jphotochem.
Nazeeruddin et al., "Conversion of Light to Electricity by cis-$X_2Bis(2,2'$-bipyridyl-4,4'-dicarboxylate)ruthenium(II) Charge-Transfer Sensitizers ($X$ = Cl-,Br-, I-, CN-, and SCN-) on Nanocrystalline $TiO_2$ Electrodes", 1993, J. Am. Chem. Soc., pp. 6382-6390, vol. 115, No. 14.
Plater et al., "A new synthetic route to doner-acceptor porphyrins", Jan. 2002, pp. 2405-2413, Tetrahedron 58.
Wang et al., "Efficient Light Harvesting by Using Green Zn-Porphyrin-Sensitized Nanocrystalline $TiO_2$ Films", May 2005, pp. 15397-15409, J. Phys. Chem. B, vol. 109, No. 32.
Susumu and Therien, "Decoupling Optical and Potentiometric Band Gaps in π-Conjugated Materials", Mar. 2002, pp. 8550-8552, J. Am. Chem. Soc., vol. 124, No. 29.
Zhao et al., "Design and synthesis of stable triarylamines for hole-transport applications", Apr. 2001, pp. 4421-4424, Tetrahedron Letters 42.

* cited by examiner

*Primary Examiner* — Paul V. Ward
(74) *Attorney, Agent, or Firm* — Muncy, Geissler, Olds & Lowe, PLLC

(57) ABSTRACT

The embodiments described herein relate to photosensitizer dyes for dye-sensitized solar cell (DSSC) devices. In one example, a series of photosensitizer dyes for DSSC devices that have a high absorption coefficient and conversion efficiency, lower cost and better safety, are provided. The photosensitizer dyes are porphyrin-based zinc (Zn) complexes.

24 Claims, 1 Drawing Sheet

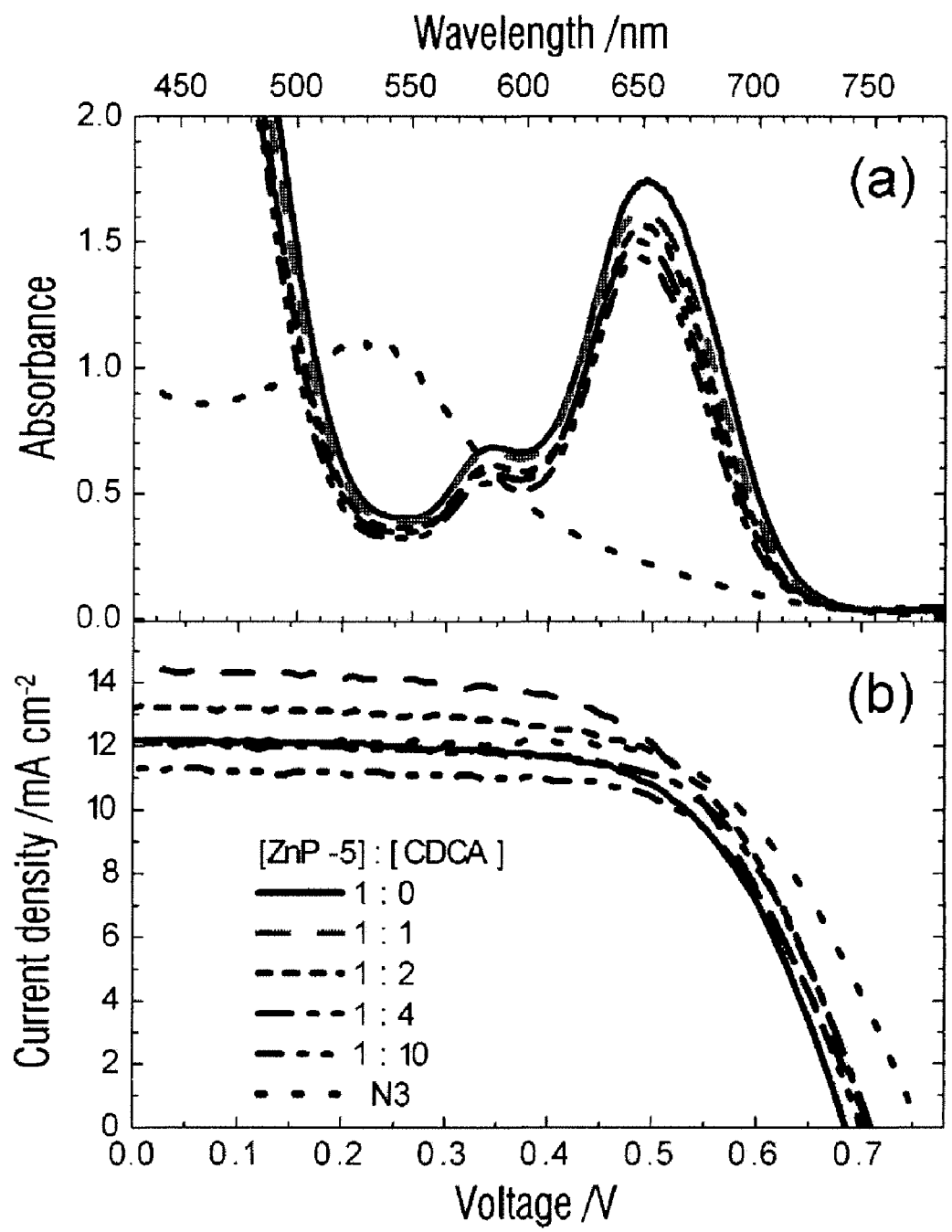

PORPHYRIN-BASED PHOTOSENSITIZER DYES FOR DYE-SENSITIZED SOLAR CELLS

CROSS-REFERENCE TO RELATED APPLICATION

This application claims the priority benefit of Taiwan application serial no. 97144426, filed on Nov. 17, 2008. All disclosure thereof is incorporated herein by reference.

BACKGROUND OF THE INVENTION

The present invention relates to a solar cell material. More specifically, the present invention relates to a porphyrin-based photosensitizer dye for dye-sensitized solar cells.

Various research studies have been carried out in an attempt to develop alternative energy sources that can replace conventional fossil fuels and solve an approaching energy crisis. Virtually inexhaustible solar energy has attracted a great deal of notice among the alternative energy sources such as wind power, atomic power, and solar power. Solar cells, or photovoltaic cells (PV cells), are considered as a major candidate for obtaining energy from the sun, since they can convert sunlight directly to electricity, provide long term power at a low operation cost, and be free of pollution associated with energy generation.

Recently, Grätzel and O'Regan have proposed a new type of solar cells known as dye-sensitized solar cells (DSSC), which have drawn much attention because they present a highly promising alternative to conventional silicon based solar cells. In nanocrystalline $TiO_2$ solar cells sensitized with a dye, poly-pyridyl ruthenium (Ru) complexes are used as photosensitizer dyes. The advantages of using such Ru complexes are that they have broad absorption in the near UV/visible regions, and appropriate excited-state oxidation potential for electron injection into the conduction band of $TiO_2$. However, on one hand, in the visible region, the absorption coefficient of poly-pyridyl Ru complexes is not large enough; on the other hand, the cost, rarity, and environmental issues of Ru complexes also limit their wide application.

It is known that in the photosynthetic cores of bacteria and plants, solar energy is collected by porphyrin-based chromophores and the captured radiant energy is efficiently converted to chemical energy. In view of such inspiration, porphyrin and phthalocyanine derivatives have been synthesized and used for photovoltaic solar cells. Thus, various porphyrin derivatives can be used to develop cheaper and safer photosensitizer dyes with a high absorption coefficient in the visible region.

SUMMARY OF THE INVENTION

An objective of the present invention is to provide a series of photosensitizer dyes for DSSC devices that have a high absorption coefficient and conversion efficiency, lower cost, and better safety.

To achieve the objective mentioned above, the present invention provides a series of photosensitizer dyes for DSSC devices, wherein the photosensitizer dyes are porphyrin-based zinc (Zn) complexes represented by the following general formulae (100) and (200):

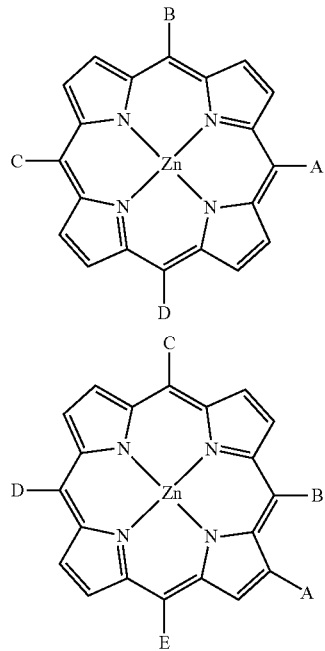

wherein A represents one of the following general formulae (111)~(118),

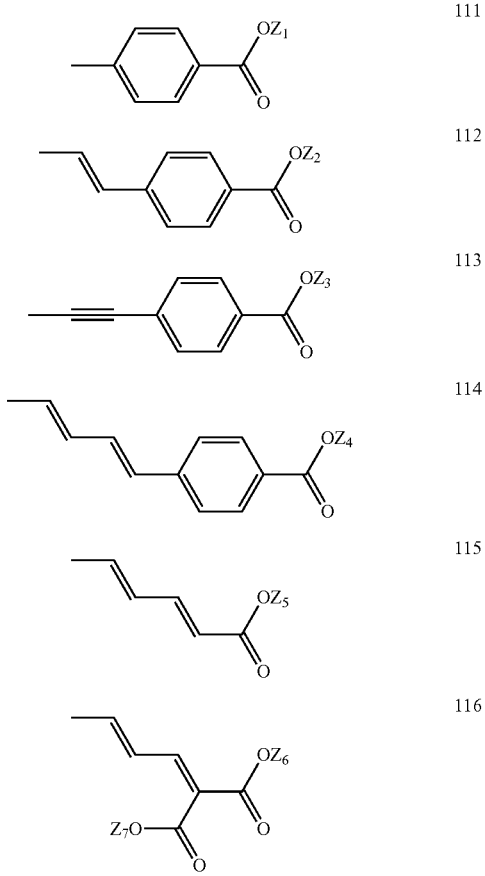

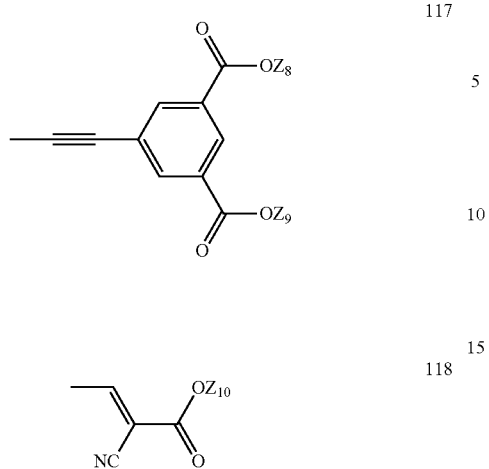

117

118 wherein $Z_1 \sim Z_{10}$ independently represent a hydrogen atom (H), lithium (Li), sodium (Na), or tetra-alkyl ammonium group represented by the following general formula (120), $$X_3-\overset{\overset{X_2}{|}}{\underset{\underset{X_4}{|}}{N}}{}^{\oplus}-X_1$$

120 wherein $X_1 \sim X_4$ independently represent $C_mH_{2m+1}$ (m=1~6), and B, C, D, and E are the same or different, and independently represented by one of the following general formulae (131)~(140):

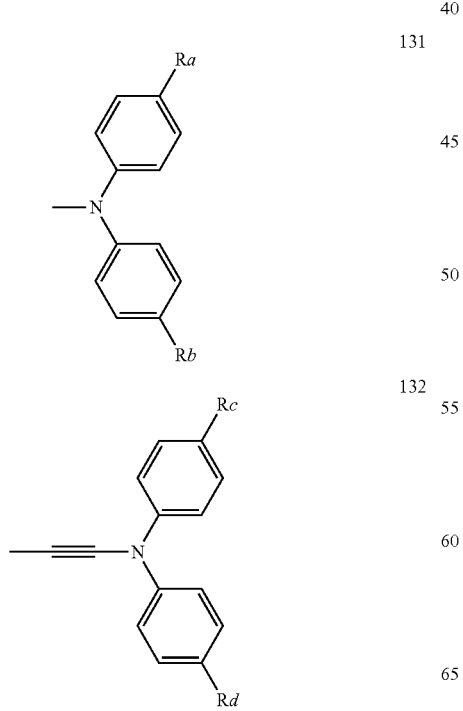

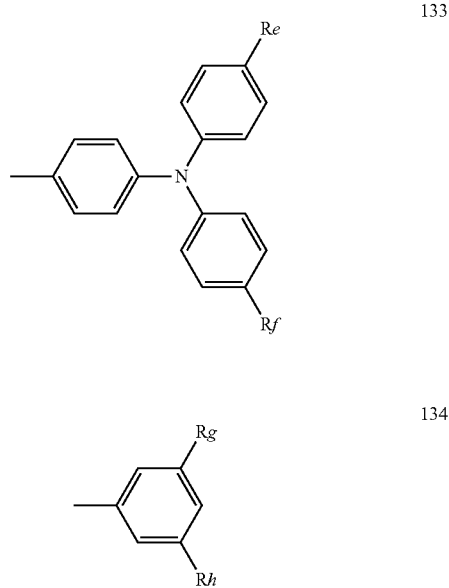

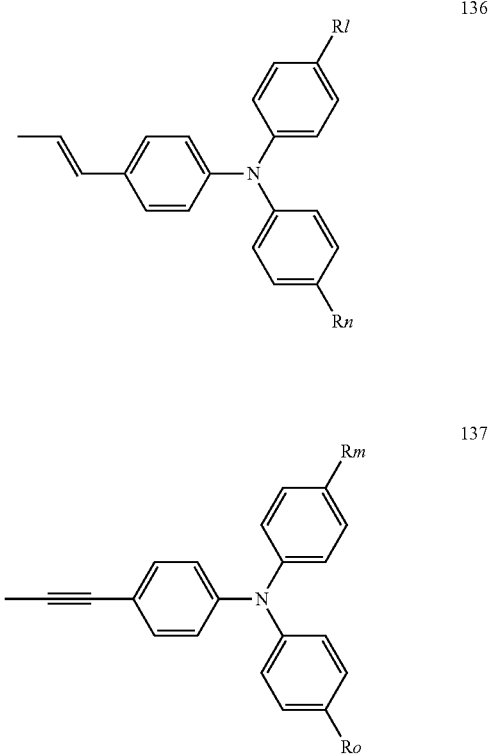

-continued

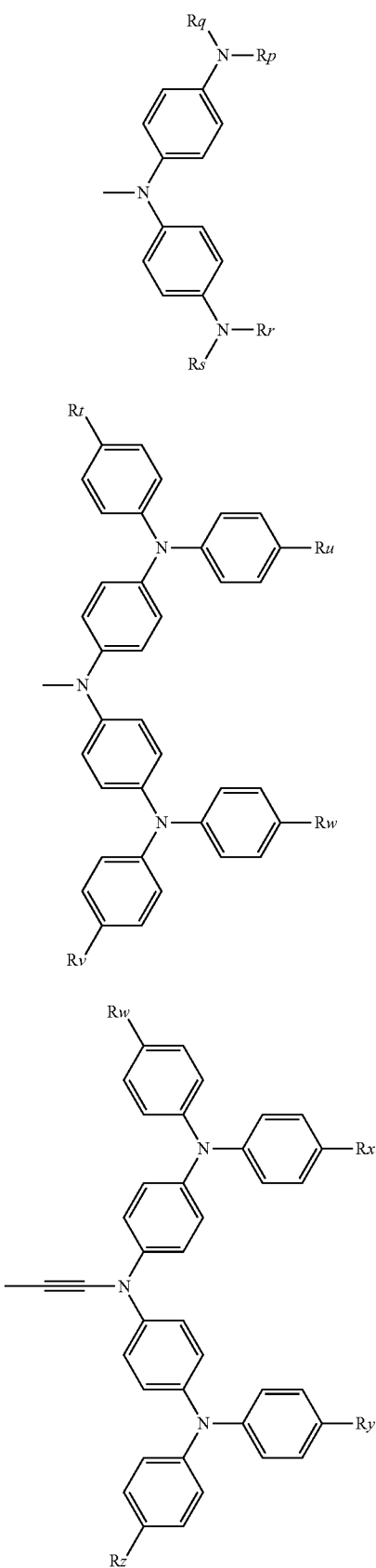

wherein $R_a$~$R_z$ are independently selected from the group consisting of H, $C_mH_{2m+1}$ (m=1~15), $OC_pH_{2p+1}$ (p=1~15), $CH_2[OC_2H_4]_nOCH_3$ (n=1~30), and $[OC_2H_4]_qOCH_3$ (q=1~30).

BRIEF DESCRIPTION OF THE DRAWINGS

FIG. 1(a) is the visible absorption spectra of the ZnP-5/$TiO_2$ films and N3/$TiO_2$ film.

FIG. 1(b) is the IV curves of the corresponding DSSC devices in FIG. 1(a).

DETAILED DESCRIPTION OF THE PREFERRED EMBODIMENTS

The technical contents, features, and effect of the present invention will be presented in more detail with reference to the following preferred embodiments thereof. In the following description, numerous specific details are set forth in order to provide a thorough understanding of the present invention. It will be apparent, however, to one skilled in the art, that the present invention may be practiced without some or all of these specific details. In other instances, well known chemical reactions and/or chemical structures have not been described in detail in order to not unnecessarily obscure the present invention.

For DSSC devices, the efficiency of photoelectric conversion depends upon the structure of the photosensitizer dyes and how the photosensitizer dyes are attached to the surface of a semiconductor such as titanium oxide ($TiO_2$). The present invention provides numerous porphyrin-based photosensitizer dyes, in which the porphyrin rings have anchoring groups for attaching to the semiconductor surface. In one embodiment, the anchoring group comprises a carboxyl group —COOH or a carboxylate anion —COO—. In order to increase the absorption of the porphyrin rings in the visible region, several substituents may be attached thereto for expanding the π-conjugation system, which causes a red shift and broadening of both Soret and Q bands in the absorption spectra. In one embodiment, the substituents are electron-donating groups.

The efficiency of sensitized photocurrent generation decreases due to the formation of dye aggregates on the semiconductor surface. To inhibit that aggregation, bulky substituents are introduced into the porphyrin rings, such as 3,5-di-tert-butylphenyl groups. However, the steric hindrance of the bulky substituents can impede adsorption of photosensitizer dyes onto the semiconductor surface. Thus, the porphyrin ring and the anchoring group are connected with a proper bridging unit, which provides a longer anchoring group promoting the adsorption onto the semiconductor surface and facilitates electron transfer from the excited dye molecules to the semiconductor surface. In one embodiment, the bridging unit is an ethyne linker. Besides, a co-adsorbate for the dye loading can be used to prevent aggregation of the photosensitizer dyes. In one embodiment, the co-adsorbate is chenodeoxycholic acid (CDCA).

In view of the above, the present invention provides a series of photosensitizer dyes for DSSC devices, in which the photosensitizer dyes are porphyrin-based Zn complexes represented by the following general formula (100) or (200):

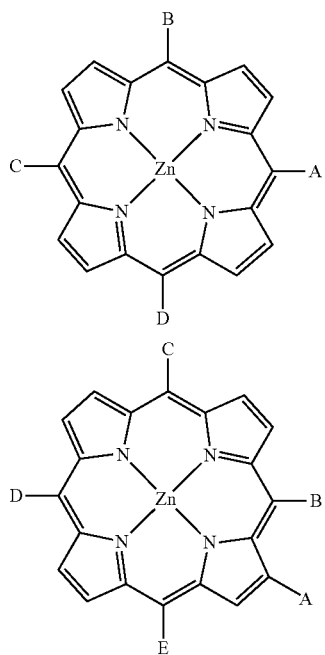

wherein A is used as the anchoring group and selected from the group represented by general formulae (111)~(118),

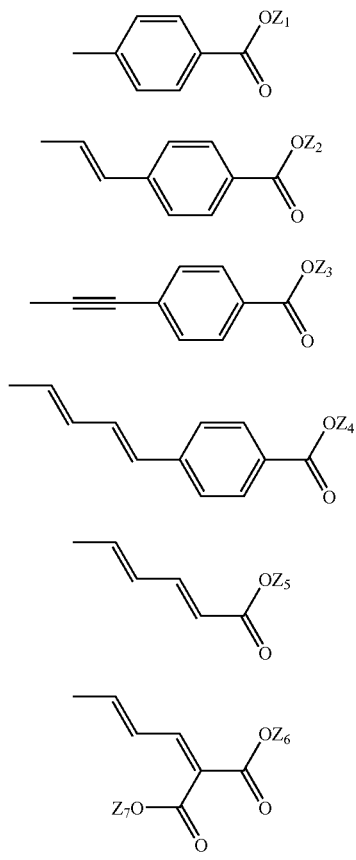

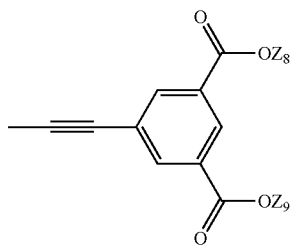

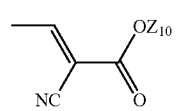

wherein $Z_1 \sim Z_{10}$ independently represent a hydrogen atom (H), lithium (Li), sodium (Na), or tetra-alkyl ammonium group represented by the following general formula (120),

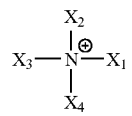

wherein $X_1 \sim X_4$ independently represent $C_mH_{2m+1}$ (m=1~6), and B, C, D, and E which can be the same or different are independently represented by one of the following general formulae (131)~(140):

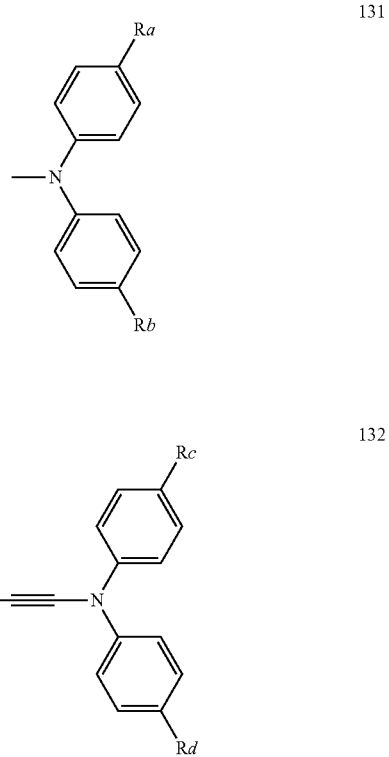

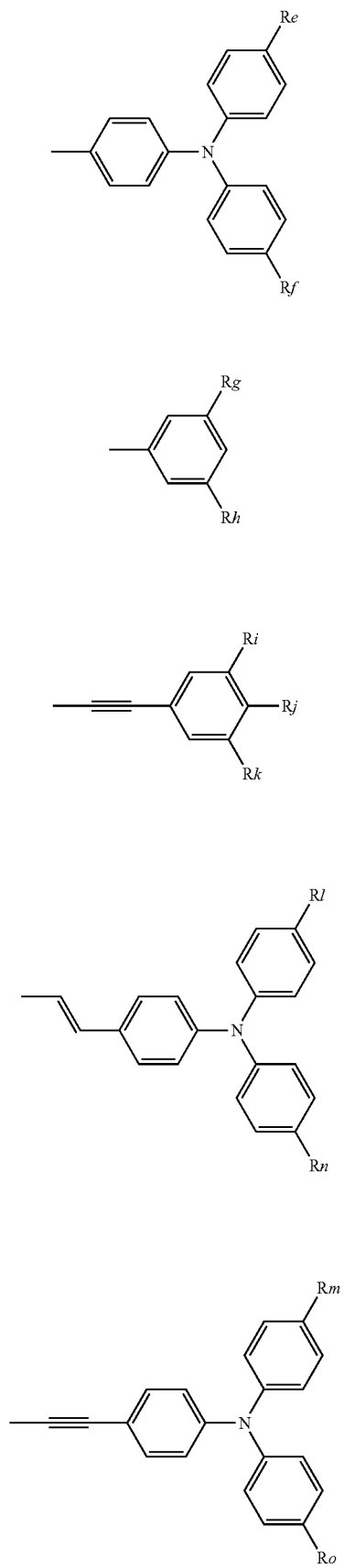

wherein $R_a\sim R_z$ are independently selected from the group consisting of H, $C_mH_{2m+1}$ (m=1~15), $OC_pH_{2p+1}$ (p=1~15), $CH_2[OC_2H_4]_nOCH_3$ (n=1~30), and $[OC_2H_4]_qOCH_3$ (q=1~30).

The synthesis of porphyrin-based photosensitizer dyes 1~12 of the present invention will be described in the following embodiments. It is to be noted that the following description should be regarded as illustrative rather than restrictive.

1

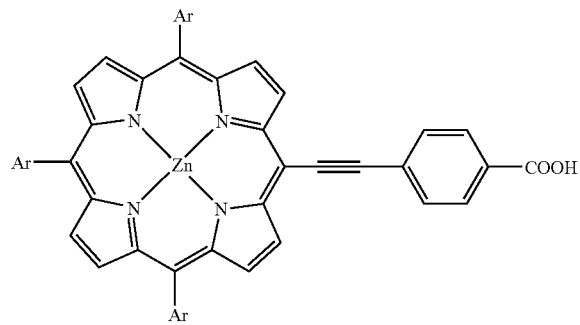

2

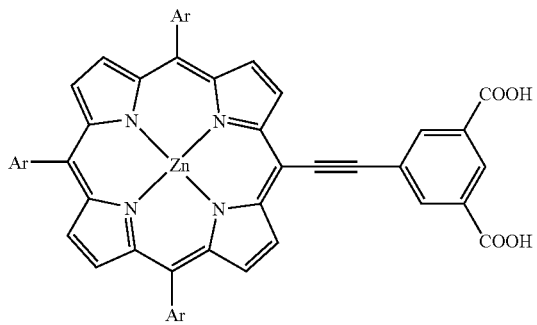

3

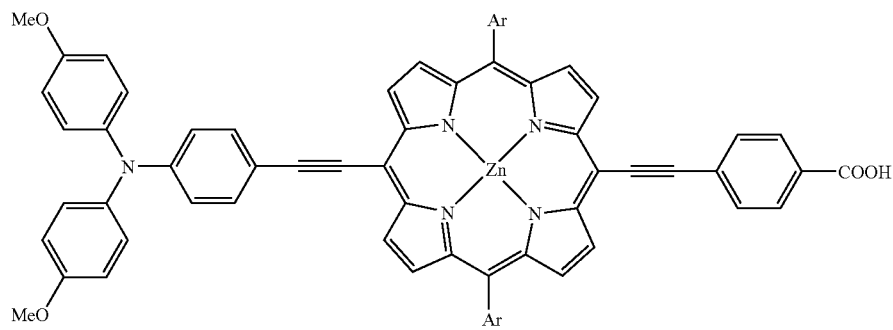

4

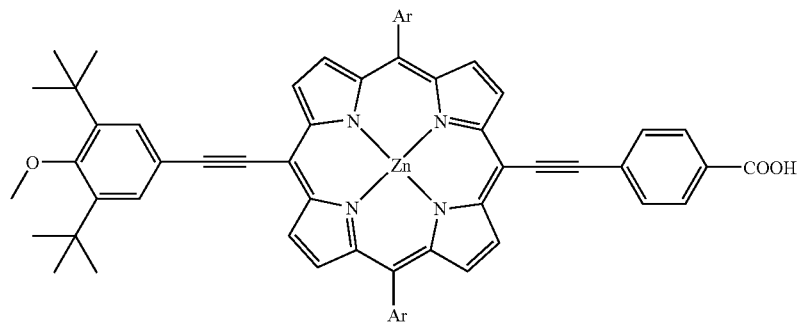

5

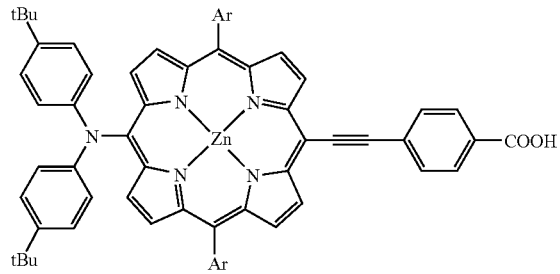

6

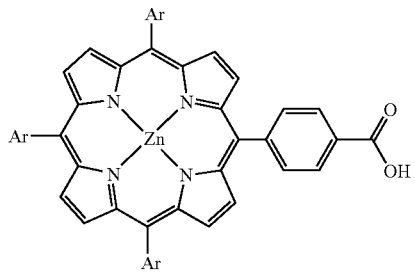

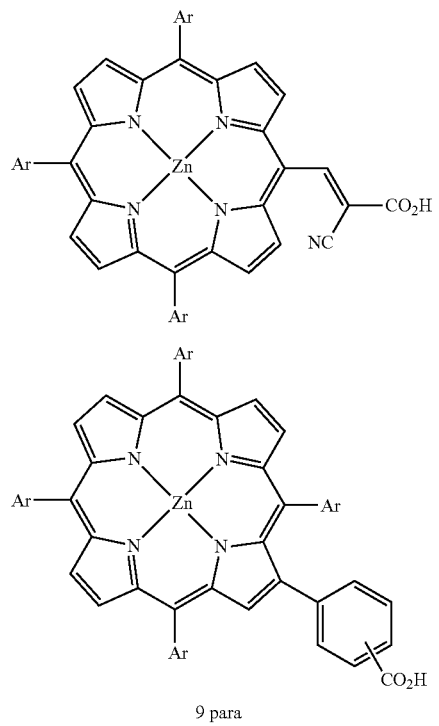
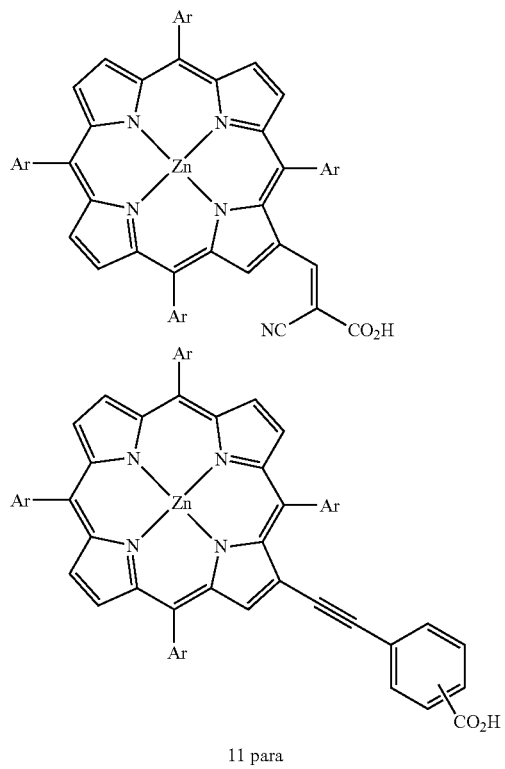
9 para
10 meta
11 para
12 meta
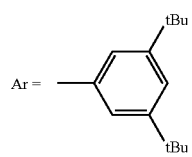
First Embodiment
The Synthesis of Photosensitizer Dye 5
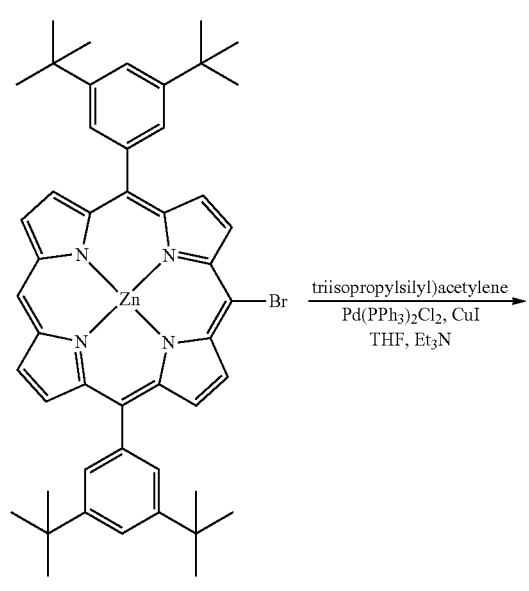
31
-continued
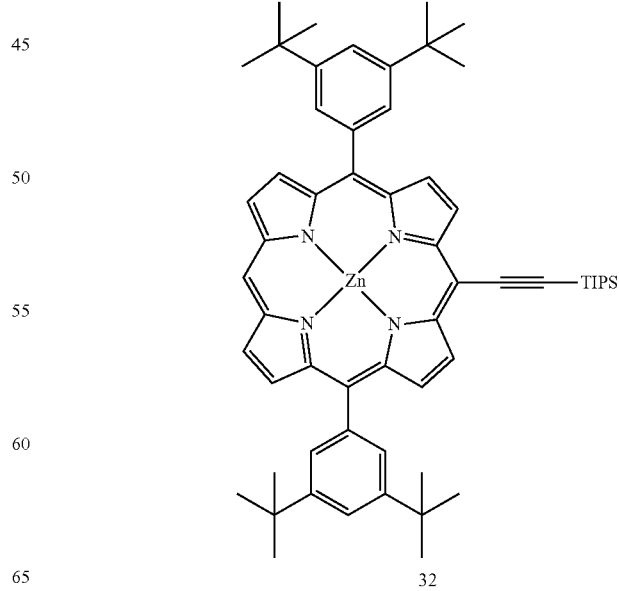
32

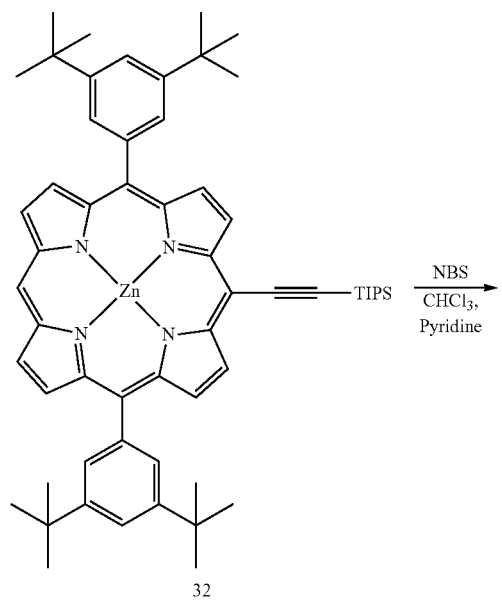
32
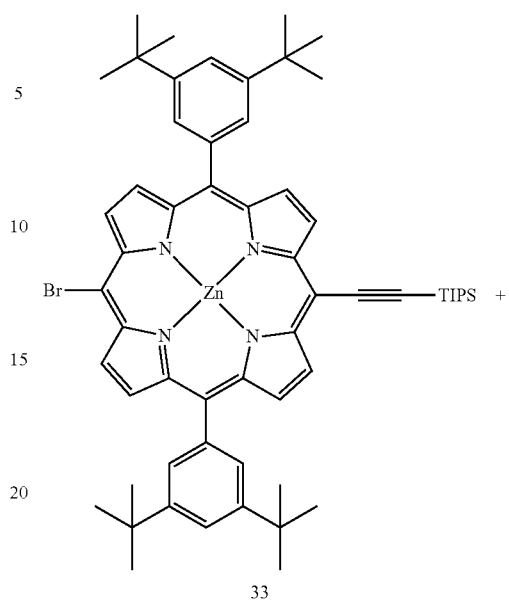
33
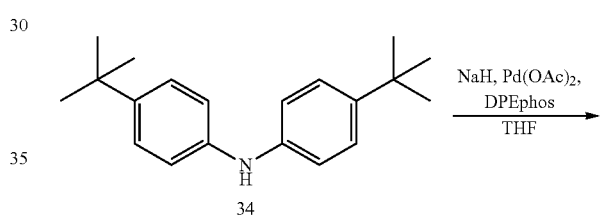
34
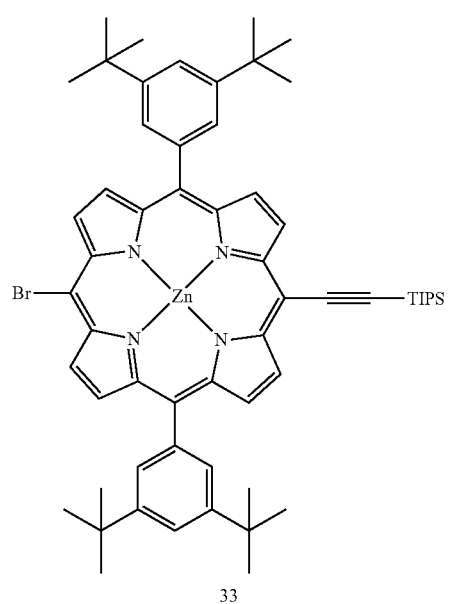
33
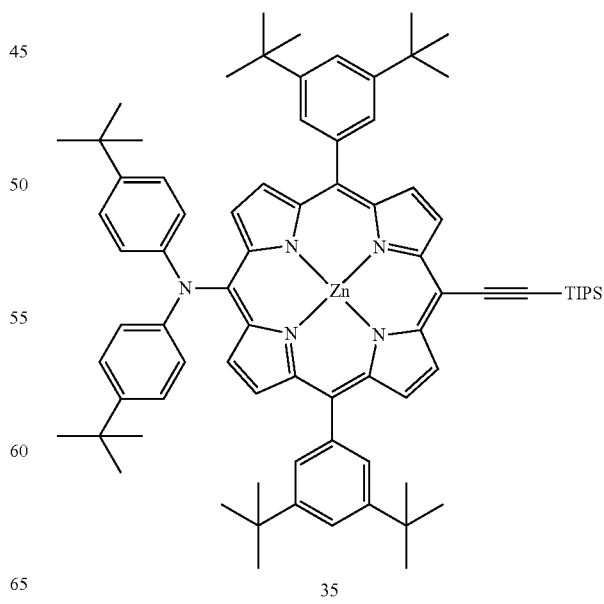
35

-continued

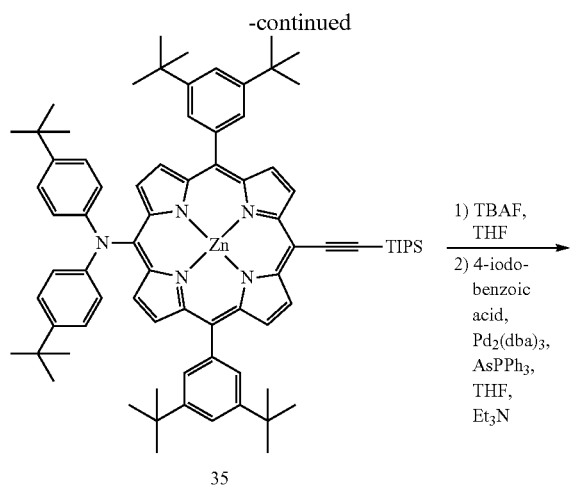

35

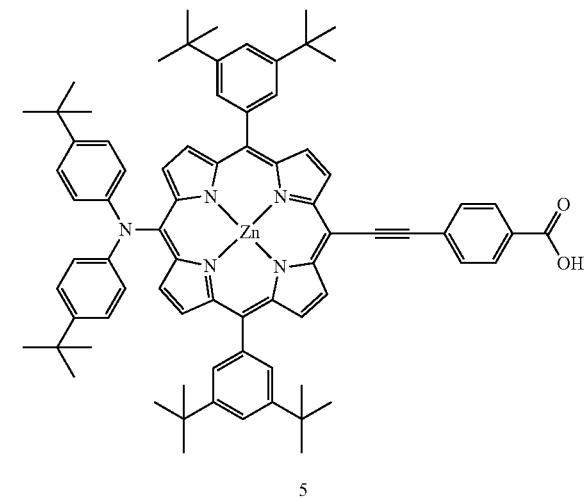

5

The chemical reactions listed above are those occur during the synthesis of porphyrin-based photosensitizer dye 5 (referred to as ZnP-5, hereinafter). 373 mg of porphyrin compound 31 (Ka, J. W. et al., *Tetrahedron Lett.* 2000, 41, 4609; Plater, M. J. et al., *Tetrahedron*, 2002, 58, 2405; and Susumu, K. et al., *J. Am. Chem. Soc.* 2002, 124, 8550) was placed in a dry two-necked flask equipped with a stirring bar at the presence of nitrogen gas, followed by adding 80 mL of dry tetrahydrofuran (THF) and 26.8 mL of dry triethylamine ($Et_3N$) thereinto and mix them well. Then the mixture was deoxygenated with nitrogen for 10 minutes. After that, 32.1 mg of bis(triphenylphosphine)palladium(II) chloride ($Pd(PPh_3)_2Cl_2$, Strem Chemicals, Inc.), 8.7 mg of cuprous iodide (CuI, Strem Chemicals, Inc.), and 0.67 mL of (triisopropylsilyl)acetylene (Acros Organics, Inc.) were added into the flask. The mixture was heated to be refluxed for 2 hours and then cooled to ambient temperature. The solvents were removed under reduced pressure, and the residue was purified by column chromatograph (packed with silica gel) using a $CH_2Cl_2$/n-hexane solution (1:4, v/v) as eluent. Recrystallization was then performed using $CH_2Cl_2/CH_3OH$, thus resulting in 341.4 mg of porphyrin 32 with the yield of 80%.

100 mg of porphyrin 32 was placed in a two-necked flask equipped with a stirring bar at the presence of nitrogen gas, then 65 mL of dry chloroform ($CHCl_3$) and 6.5 mg of dry pyridine were added thereinto. With the stirring bar activated, the mixture was deoxygenated with nitrogen for 10 minutes. 37 mg of N-bromosuccinimide (NBS, Acros Organics, Inc.) was added to undergo bromination for 10 minutes, and then the reaction was terminated by adding 1.0 mL of acetone. The solvents were removed under reduced pressure, and the residue was purified by column chromatograph (packed with silica gel) using a $CH_2Cl_2$/n-hexane solution (1:4, v/v) as eluent. Recrystallization was then performed using $CH_2Cl_2/CH_3OH$, thus leading to 95 mg of porphyrin 33 with the yield of 88%.

50 mg of compound 34 (Zhao, H. et al., *Tetrahedron Lett.* 2001, 42, 4421) and 16.8 mg of sodium hydride (NaH) were placed in a two-necked flask equipped with a stirring bar at the presence of nitrogen, followed by adding 10 mL of dry THF and stirring the mixture for 3 minutes. Next, 50 mg of porphyrin 33, 2.2 mg of palladium(II) acetate ($Pd(OAc)_2$, Strem Chemicals, Inc.), and 8 mg of bis[(2-diphenylphosphino)phenyl]ether (DPEphos, Acros Organics, Inc.) were added thereinto. The mixture were deoxygenated with nitrogen for 10 minutes, refluxed for 5 hours, and then cooled to ambient temperature. The solvent was removed under reduced pressure, and the residue was purified by column chromatograph (packed with silica gel) using a $CH_2Cl_2$/n-hexane solution (1:4, v/v) as eluent. Recrystallization was then performed using $CH_2Cl_2/CH_3OH$, thus resulting in 30 mg of porphyrin 35 with the yield of 50%.

23.2 mg of porphyrin 35 was placed in a two-necked flask equipped with a stirring bar at the presence of nitrogen, and 4 mL of THF and 0.08 mL of tetrabutylammonium fluoride (TBAF, 1 M in THF, Acros Organics, Inc.) were added thereinto afterwards. The mixture was stirred for reaction for 30 minutes at ambient temperature. The solvent was removed under reduced pressure, and the residue was extracted using $H_2O$ and $CH_2Cl_2$. The organic layer was collected, dehydrated using anhydrous sodium sulfate, and filtered by suction. The filtrate was collected into a two-necked flask, and concentrated under reduced pressure to remove the solvent. After that, 5 mg of 4-iodobenzoic acid (Acros Organics, Inc.) was added at the presence of nitrogen, followed by adding 5 mL of dry THF and 1 mL of dry $Et_3N$. The mixture was deoxygenated with nitrogen for 10 minutes. 2.2 mg of tris(dibenzylideneacetone)dipalladium(0) ($Pd_2(dba)_3$, Strem Chemicals, Inc.) and 7 mg of triphenyl arsine ($AsPh_3$, Acros Organics, Inc.) were added. The mixture was refluxed for 2 hours and then cooled to ambient temperature. The solvent was removed under reduced pressure, and the residue was purified by column chromatograph (packed with silica gel) using a $CH_2Cl_2/CH_3OH$ solution (9:1, v/v) as eluent. Recrystallization was then performed using $CH_2Cl_2/CH_3OH$, thus leading to 14 mg of ZnP-5 with the yield of 62%.

Second Embodiment

The Synthesis of Photosensitizer Dyes 1 and 2

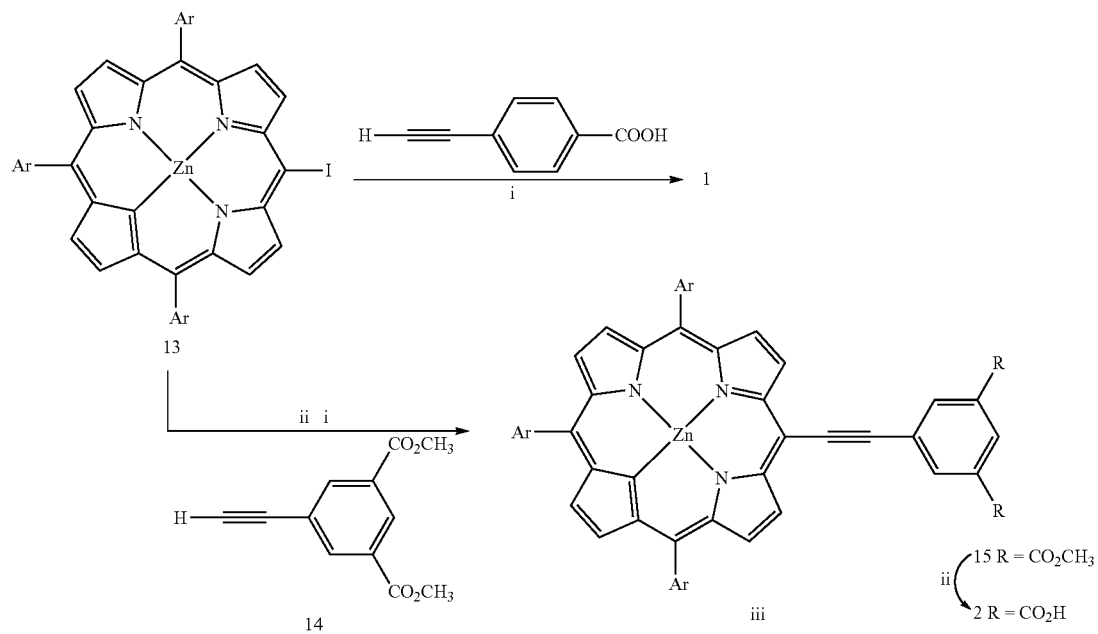

i) Pd(PPh$_3$)$_4$, CuI, THF, NEt$_3$, reflux;
ii) Pd$_2$(dba)$_3$, AsPh$_3$, THF, NEt$_3$, reflux;
iii) NaOH, THF, CH$_3$OH, reflux Referring to the above chemical equations. A mixture of porphyrinyl iodide 13 (21 mg) and 4-ethynylbenzoic acid (4.4 mg) in dry THF (2 mL) and Et$_3$N (1 mL) was prepared and deoxygenated with nitrogen for 10 minutes, followed by adding palladium(0) tetra(triphenylphosphine) (Pd(PPh$_3$)$_4$, 4.6 mg) and CuI (0.4 mg) thereinto. The mixture was refluxed under nitrogen for 2 hours. The solvent was removed by vacuum, and the residue was purified by column chromatograph (packed with silica gel) using a CH$_2$Cl$_2$/n-hexane solution (9:1, v/v) as eluent. Recrystallization was then performed using CH$_2$Cl$_2$/CH$_3$OH, thus resulting in 19.4 mg of photosensitizer dye 1 (ZnP-1) with the yield of 90%.

Besides, a mixture of porphyrinyl iodide 13 (10 mg) and dimethyl 5-ethynyl-isophthalate 14 (6.5 mg) in dry THF (5 mL) and Et$_3$N (1 mL) was prepared and deoxygenated with nitrogen for 10 minutes, followed by adding Pd$_2$(dba)$_3$ (2.2 mg) and AsPh$_3$ (6 mg) thereinto. The mixture was refluxed under nitrogen for 1 hour. The solvent was removed by vacuum, and the residue was purified by column chromatograph (packed with silica gel) using a CH$_2$Cl$_2$/n-hexane solution (4:6, v/v) as eluent. Recrystallization was then performed using CH$_2$Cl$_2$/CH$_3$OH, thus leading to 10.4 mg of porphyrin 15 with the yield of 90%.

A mixture of porphyrin 15 (23 mg) and NaOH (0.5 M, 1 mL) in THF (5 mL) and CH$_3$OH (2 mL) was heated and refluxed for 4 hours. After being cooled to 25° C., the solution was extracted using H$_2$O and CH$_2$Cl$_2$. The organic layer was collected and then washed sequentially using HCl (1%, 10 mL) and H$_2$O (10 mL*3). The solvent was removed by vacuum. Recrystallization was then performed using CH$_2$Cl$_2$/CH$_3$OH, thus resulting in 22.2 mg of photosensitizer dye 2 (ZnP-2) with the yield of 99%.

Third Embodiment

The Synthesis of Photosensitizer Dyes 3 and 4

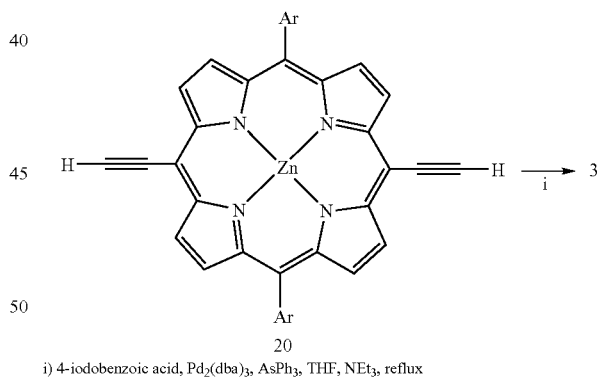

i) 4-iodobenzoic acid, Pd$_2$(dba)$_3$, AsPh$_3$, THF, NEt$_3$, reflux

A mixture of N,N-bis(4-methoxyphenyl)-4'-iodophenylamine 19 (10.4 mg), 4-iodobenzoic acid (4 mg), and porphyrin 20 (16 mg) in dry THF (10 mL) and Et$_3$N (2 mL) was prepared and deoxygenated with nitrogen for 10 minutes, followed by adding Pd$_2$(dba)$_3$ (4.4 mg) and AsPh$_3$ (12 mg) thereinto. The mixture was heated and refluxed under nitrogen for 2.5 hours. The solvent was removed by vacuum, and the residue was purified by column chromatograph (packed with silica gel) using a CH$_2$Cl$_2$/CH$_3$OH solution (9:1, v/v) as eluent. Recrystallization was then performed using CH$_2$Cl$_2$/CH$_3$OH, leading to 9.8 mg of photosensitizer dye 3 (ZnP-3) with the yield of 40%.

Similarly, a mixture of 5-iodo-2-methoxy-1,3-di-tert-butylbenzene (8.3 mg), 4-iodobenzoic acid (4 mg), and porphyrin 20 (16 mg) in dry THF (10 mL) and $Et_3N$ (2 mL) was prepared and deoxygenated with nitrogen for 10 minutes, followed by adding $Pd_2(dba)_3$ (4.4 mg) and $AsPh_3$ (12 mg) thereinto. The mixture was heated and refluxed under nitrogen for 4 hours, and then purified according to a method similar to that for ZnP-3 to obtain 8.2 mg of photosensitizer dye 4 (ZnP-4) with the yield of 36%.

Fourth Embodiment

The Synthesis of Photosensitizer Dye 6

Photosensitizer dye 6 can be prepared according to a method similar to that disclosed in the literature (C. Luo et al., *J. Am. Chem. Soc.* 2000, 122, 6535).

Fifth Embodiment

The Synthesis of Photosensitizer Dye 7

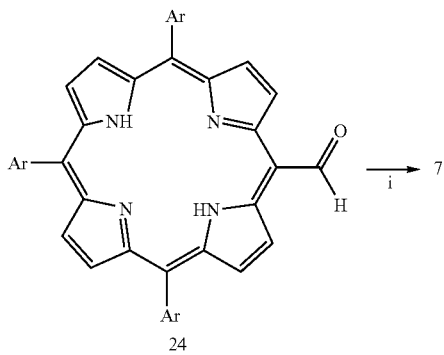

24 i) Piperidine, acetonitrile, cyanoacetic acid, reflux; then $Zn(OAc)_2 \cdot 2H_2O$, $CH_3OH$, $CH_2Cl_2$, room temperature Referring to the above chemical equation, a mixture of compound 24 (36 mg), cyanoacetic acid (18 mg), piperidine (0.13 mL), and acetonitrile (10 mL) was heated and refluxed for 6 hours. The solvent was removed by vacuum, and the residue was purified by column chromatograph (packed with silica gel) using a $CH_2Cl_2/CH_3OH$ solution (9:1, v/v) as eluent. Subsequently, zinc insertion was performed using zinc acetate dihydrate ($Zn(OAc)_2 \cdot 2H_2O$), thus resulting in 41 mg of photosensitizer dye 7 (ZnP-7) with the yield of 99%.

Sixth Embodiment

The Synthesis of Photosensitizer Dye 8

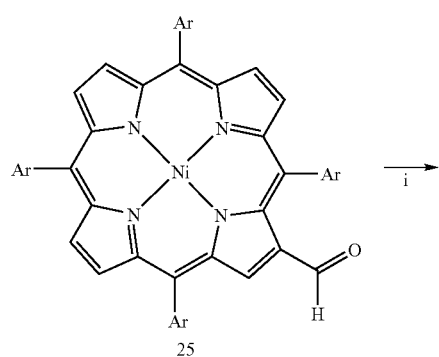

25

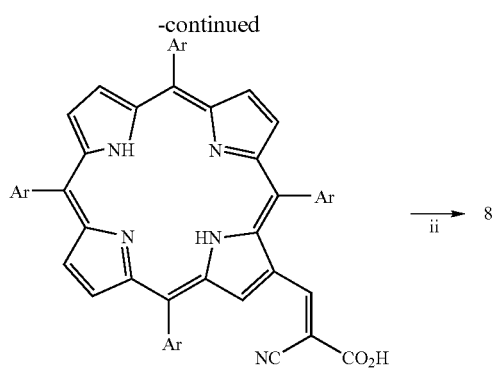

26 i) Piperidine, acetonitrile, cyanoacetic acid, reflux; then $H_2SO_4$.
ii) $Zn(OAc)_2 \cdot 2H_2O$, $CH_3OH$, $CH_2Cl_2$, room temperature Referring to the above chemical equation, a mixture of porphyrin 25 (45.8 mg), cyanoacetic acid (18 mg), piperidine (0.13 mL), acetonitrile (5 mL), and dichloroethane (5 mL) was heated and refluxed for 6 hours. The solvent was removed by vacuum, and the residue was purified by column chromatograph (silica gel) using $CH_2Cl_2/CH_3OH$ (9/1) as eluent. Demetallation was performed using a mixture of $H_2SO_4$ (2 mL) and $CH_2Cl_2$ (10 mL), followed by adding $H_2O$ (10 mL) and $CH_2Cl_2$ (10 mL) and collecting the organic layer. The solvent was removed in vacuo to give compound 26, which was then subjected to zinc insertion using $Zn(OAc)_2 \cdot 2H_2O$. Recrystallization of the crude product from $CH_2Cl_2/CH_3OH$ gave photosensitizer dye 8 (ZnP-8, 33 mg, 70%).

Seventh Embodiment

The Synthesis of Photosensitizer Dyes 9, 10, 11, and 12

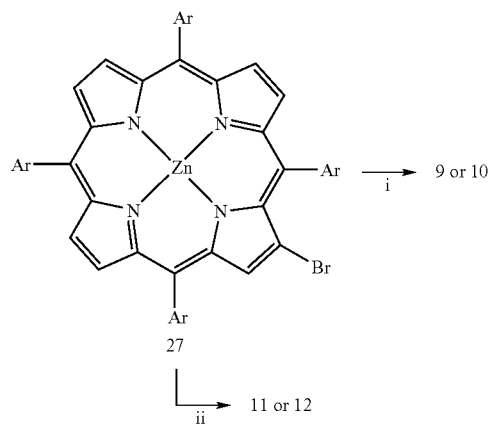

27 i) methylbenzoate boronic acid, $K_2CO_{3(aq)}$, $Pd(PPh_3)_4$, ethandiol methyl ester, reflux; then NaOH, THF, $CH_3OH$, reflux.
ii) ethynylbenzoic acid, $Pd_2(dba)_3$, $AsPh_3$, THF, $NEt_3$, reflux.

In light of the disclosure of J. P. C. Tomé et al., *Eur. J. Org. Chem.* 2006, 257, bromination of 5,10,15,20-tetrakis(3,5-di-tert-butylphenyl)porphyrin with NBS followed by a zinc insertion reaction gives porphyrin 27.

Referring to the above chemical equation, a mixture of porphyrin 27 (21.3 mg), 4-methylbenzoate boronic acid (20 mg), and aqueous $K_2CO_3$ (1 M, 0.1 mL) in ethanediol methyl ether (10 mL) was deoxygenated with nitrogen for 10 minutes, followed by adding $Pd(PPh_3)_4$ (8 mg) thereinto. The mixture was heated and refluxed under nitrogen for 18 hours.

The solvent was removed by vacuum, and the residue was purified by column chromatograph (packed with silica gel) using a $CH_2Cl_2$/n-hexane solution (4:6, v/v) as eluent. Next, recrystallization was performed using $CH_2Cl_2/CH_3OH$, thus 11 mg of an intermediate was obtained with the yield of 45%. According to a method similar to that for ZnP-2, the intermediate was hydrolyzed under an alkaline condition (NaOH/THF/$CH_3OH$) and then purified to obtain photosensitizer dye 9 (ZnP-9) with the yield of 99%.

Besides, a mixture of porphyrin 27 (28 mg), 3-methylbenzoate boronic acid (20 mg), and aqueous $K_2CO_3$ (1 M, 0.1 mL) in ethanediol methyl ether (10 mL) was deoxygenated with nitrogen for 10 minutes, followed by adding $Pd(PPh_3)_4$ (8 mg) thereinto. The mixture was heated and refluxed under nitrogen for 18 hours. The solvent was removed by vacuum, and the residue was purified by column chromatograph (packed with silica gel) using a $CH_2Cl_2$/n-hexane solution (4:6, v/v) as eluent. Recrystallization was performed using $CH_2Cl_2/CH_3OH$, thus 12.4 mg of an intermediate was obtained with the yield of 50%. According to a method similar to that for ZnP-2, the intermediate was hydrolyzed under an alkaline condition (NaOH/THF/$CH_3OH$) and then purified to obtain photosensitizer dye 10 (ZnP-10, 99%).

A mixture of porphyrin 27 (24 mg), 4-ethynylbenzoic acid (29.2 mg) in dry THF (10 mL) and $Et_3N$ (2 mL) was deoxygenated with nitrogen for 10 minutes, followed by adding $Pd_2(dba)_3$ (9.2 mg) and $AsPh_3$ (24.5 mg). The mixture was refluxed under nitrogen for 24 hours. The solvent was removed in vacuo, and the residue was purified by column chromatograph (silica gel) using $CH_2Cl_2/CH_3OH$ (9/1) as eluent. Recrystallization from $CH_2Cl_2/CH_3OH$ gave photosensitizer dye 11 (ZnP-11, 7.6 mg, 30%).

A mixture of porphyrin 27 (24 mg), 3-ethynylbenzoic acid (29.2 mg) in dry THF (10 mL) and $Et_3N$ (2 mL) was deoxygenated with nitrogen for 10 minutes, followed by adding $Pd_2(dba)_3$ (9.2 mg) and $AsPh_3$ (24.5 mg). The mixture was refluxed under nitrogen for 24 hours, and then purified according to a method similar to that for ZnP-11 to obtain photosensitizer dye 12 (ZnP-12, 8.3 mg, 33%).

Photosensitizer dyes ZnP-1~ZnP-12 were dissolved in a $CH_2Cl_2$/pyridine solution (100:1, v/v), and the absorption spectra thereof were determined by a UV/Vis spectrophotometer. The absorption coefficients of ZnP-1~ZnP-12 of the present invention are summarized in Table 1. Furthermore, one of the representative photosensitizer dyes in the literature is N3, which is a poly-pyridyl Ru complex disclosed by Grätzel (M. Grätzel, *J. Photochem. A*, 2004, 164, 3, and M. K. Nazeeruddin et al., *J. Am. Chem. Soc.* 1993, 115, 6382). The spectral absorption coefficient of N3 was also measured for comparison.

TABLE 1

| Photosensitizer Dye | Absorption Peak $\lambda_{max}$/nm (Absorption Coefficient $\epsilon/10^3 \, M^{-1}cm^{-1}$) |
|---|---|
| ZnP-1 | 445 (282), 579 (9.5), 636 (24.8) |
| ZnP-2 | 445 (231), 582 (8.2), 632 (19.4) |
| ZnP-3 | 451 (117), 680 (30.6) |
| ZnP-4 | 454 (283), 668 (51.0) |
| ZnP-5 | 448 (194), 601 (8.3), 654 (29.7) |
| ZnP-6 | 430 (616), 565 (20.7), 605 (14.7) |
| ZnP-7 | 455 (106), 571 (7.1), 636 (8.4) |
| ZnP-8 | 451 (129), 564 (11.7), 613 (11.1) |
| ZnP-9 | 434 (326), 567 (12.9), 607 (7.7) |
| ZnP-10 | 433 (409), 566 (16.3), 609 (10.7) |
| ZnP-11 | 442 (348), 574 (21.0), 618 (13.0) |
| ZnP-12 | 444 (375), 575 (25.1), 618 (16.3) |
| N3 | 314 (482), 389 (140), 534(142) |

Then, DSSC devices using the photosensitizer dyes of the present invention were fabricated and measured for the photovoltaic properties thereof. ZnP-5 is exemplified herein as a photosensitizer dye. The $TiO_2$ nanoparticles having a diameter around 20 nm prepared with a sol-gel method were screen-printed onto the F-doped $SnO_2$ (FTO) glass substrate. Crystallization of $TiO_2$ film (thickness ~9 μm and active area 0.16 $cm^2$) was performed by two-stage annealing: heating the $TiO_2$ film at 450° C. for 5 minutes, followed by another heating at 500° C. for 30 minutes. The $TiO_2$ film was then immersed in an aqueous solution of $TiCl_4$ (50 mM, 70° C.) for 30 minutes, followed by the same two-stage thermal treatment for final annealing of the electrode. In one embodiment, the electrode was then immersed in the ZnP-5/ethanol solution (20 mM, 25° C.) containing CDCA (20 mM) for 2 hours for dye loading onto the $TiO_2$ film. The Pt counter electrodes were prepared by spin-coating $H_2PtCl_6$ solution onto the FTO glass and heating at 400° C. for 15 minutes. To prevent a short circuit, the two electrodes were assembled into a cell of sandwich type and sealed with a hot-melt film (SX1170, Solaronix, 25 μm). In light of the disclosure of Q. Wang et al., *J. Phys. Chem. B* 2005, 109, 15397, the electrolyte solution containing LiI (0.1 M), $I_2$ (0.05 M), BMII (0.6 M), 4-tert-butylpyridine (0.5 M) in a mixture of acetonitrile and valeronitrile (1:1, v/v) was introduced into the space between the two electrodes, and the fabrication of the DSSC device was complete. In this embodiment, the concentration ratio of ZnP-5 to CDCA is 1:1; however, in another embodiment, the concentration ratio of ZnP-5 to CDCA may be varied.

Besides, according to the method similar to that mentioned above, the DSSC device using N3 dye was prepared for comparison.

Then, DSSC devices using ZnP-5 and N3 were analyzed for the photovoltaic properties and visible absorption spectra thereof. Through analyzing an I-V curve with respect to ZnP-5 and. N3 by a solar simulator (Newport-Oriel 91160) having an air mass (AM) of 1.5, the performance of DSSC devices were assessed. The solar simulator uses filters and other optical components to simulate solar radiation having an AM of 1.5, and the output intensity is evenly distributed on a large area. When the DSSC device is irradiated with the solar simulator, the source meter (Keithley 2400) controlled by a computer transmits a voltage to the device, and the corresponding photocurrent is read at each step. The photoelectric conversion efficiency (η) is obtained by the relations below, $$\eta = \frac{P_{mp}}{P_{in}} = \frac{J_{mp} * V_{mp}}{P_{in}} = \frac{J_{SC} * V_{OC} * FF}{P_{in}}$$

wherein $P_{in}$ is the input radiation power, and $P_{mp}$ is the maximum output power ($=J_{mp} \times V_{mp}$), and FF indicates the fill factor defined as $$FF = \frac{J_{mp} * V_{mp}}{J_{SC} * V_{OC}}$$

wherein $J_{SC}$ is the short circuit current density, and $V_{OC}$ is the open circuit voltage.

In this embodiment, CDCA was used as a co-adsorbate to prevent aggregation of the dyes on the TiO$_2$ surface. Besides, the concentration ratio of ZnP-5 to CDCA was varied as 1:0, 1:1, 1:2, 1:4, and 1:10 for seeking an optimal condition that can impede aggregation of ZnP-5 and increase the power conversion efficiency more effectively.

The measured visible absorption spectra of the ZnP-5 and the conventional N3 on the TiO$_2$ film are shown in FIG. 1(a), and the I-V curves of the corresponding DSSC devices are shown in FIG. 1(b). The photovoltaic parameters thereof are summarized in Table 2 respectively.

TABLE 2

| [ZnP-5]:[CDCA] | $J_{sc}$ (mA cm$^{-2}$) | $V_{oc}$ (mV) | FF | η (%) |
|---|---|---|---|---|
| 1:0 | 12.22 | 686 | 0.645 | 5.4 |
| 1:1 | 14.33 | 710 | 0.594 | 6.0 |
| 1:2 | 13.22 | 708 | 0.640 | 6.0 |
| 1:4 | 12.05 | 710 | 0.662 | 5.7 |
| 1:10 | 11.23 | 701 | 0.668 | 5.3 |
| N3 | 12.08 | 756 | 0.666 | 6.1 |

According to Table 2, it is concluded that when a solar simulator of AM 1.5 is employed, the DSSC devices using ZnP-5 with a ratio of 1:1 or 1:2 (ZnP-5:CDCA) have a overall conversion efficiency comparable to that using N3 dye.

As shown in FIG. 1(a), when comparing the visible absorption spectra of DSSC devices using ZnP-5 and N3, it is found that the maximum wavelength of absorption peaks for N3 is at about 530 nm, whereas the Q-band of ZnP-5 is red-shifted to 650 nm because ZnP-5 comprises one of the special groups represented by the general formulae (131)~(140) in the above. Besides, the absorption coefficient of ZnP-5 is larger than that of N3. Therefore, in the visible region, ZnP-5 has longer absorption wavelength and larger absorption coefficient than N3.

Referring back to Table 1, it is found that since the porphyrin photosensitizer dyes of the present invention comprise one of the special groups represented by the general formulae (131)~(140), they have longer absorption wavelength and larger absorption coefficient in the visible region and are particularly applicable to indoor (artificial) light sources. Furthermore, the porphyrin photosensitizer dyes of the present invention are not Ru-containing complexes, so they provide the advantages of lower cost and better safety.

While some embodiments of the present invention are described above, it is intended that the scope of the invention be limited not by this detailed description, but rather by the claims appended hereto. Besides, it is intended that the following appended claims be interpreted as including all such alterations, permutations, and equivalents as fall within the true spirit and scope of the present invention.

What is claimed is:

1. A dye for a dye-sensitized solar cell, the dye being represented by the following general formula (100):

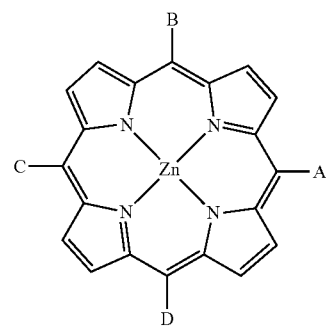

wherein A is represented by one of the following general formulae (111) to (118),

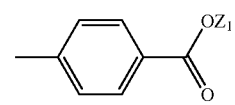

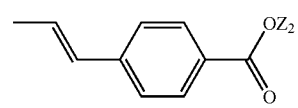

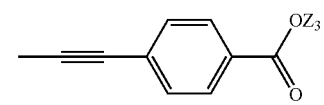

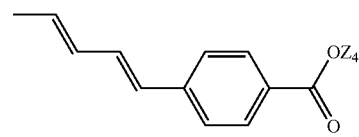

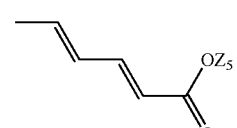

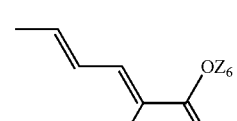

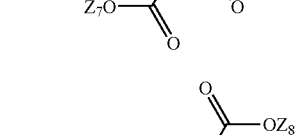

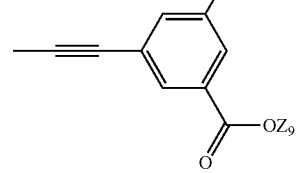

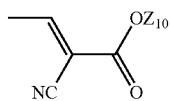
118
wherein $Z_1$ to $Z_{10}$ independently represent a hydrogen atom (H), lithium (Li), sodium (Na), or tetra-alkyl ammonium group represented by the following general formula (120),
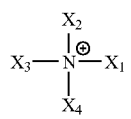
120
wherein $X_1$ to $X_4$ independently represent $C_mH_{2m+1}$ (m=1 to 6), and B, C, and D are the same or different, and independently represented by one of the following general formulae (131) to (140):
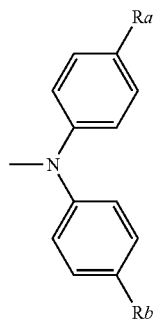
131
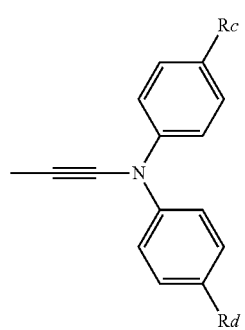
132
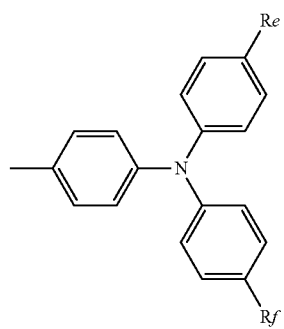
133
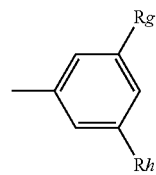
134
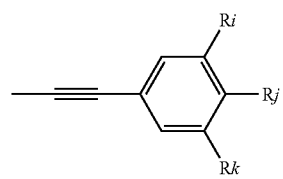
135
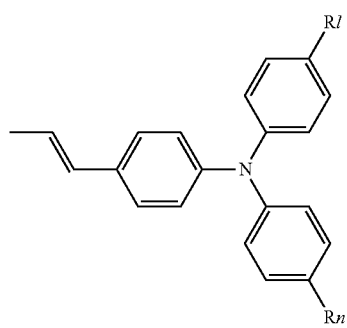
136
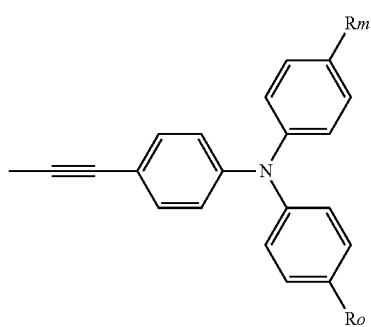
137
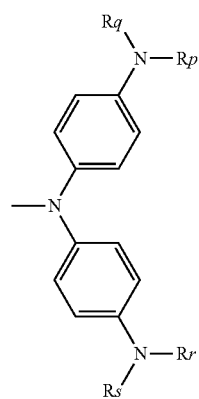
138

-continued

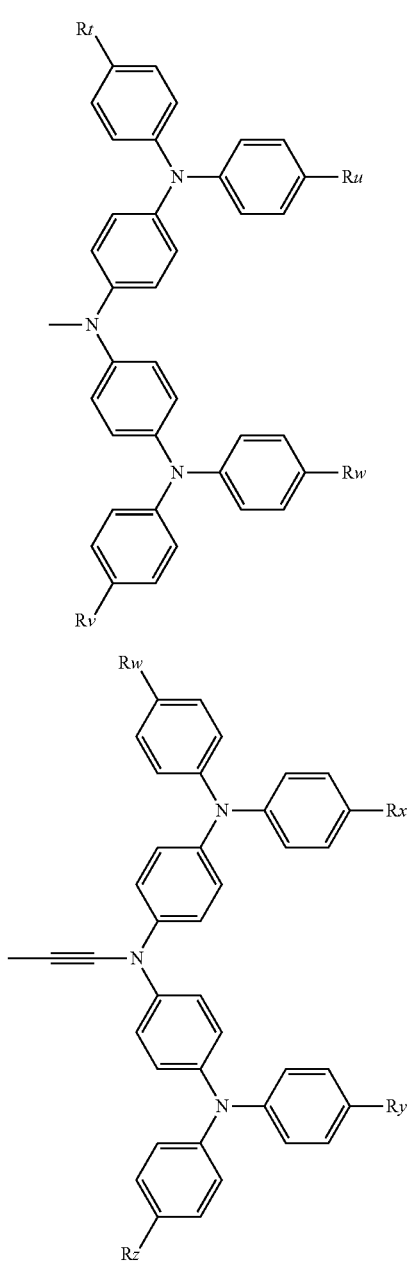

139

140 wherein $R_a$ to $R_f$ and $R_t$ to $R_z$ are independently selected from the group consisting of H, $C_mH_{2m+1}$ (m=1 to 15), $OC_pH_{2p+1}$ (p=1 to 15), $CH_2[OC_2H_4]_nOCH_3$ (n=1 to 30), and $[OC_2H_4]_qOCH_3$ (q=1 to 30), and $R_g$ and $R_h$ are independently selected from the group consisting of $C_mH_{2m+1}$ (m=1 to 15), $OC_pH_{2p+1}$ (p=1 to 15), $CH_2[OC_2H_4]_nOCH_3$ (n=1 to 30), and $[OC_2H_4]_qOCH_3$ (q=1 to 30).

2. The dye of claim 1, wherein A is represented by the general formula (113).

3. The dye of claim 2, wherein $Z_3$ represents a hydrogen atom (H).

4. The dye of claim 1, wherein B and D each are represented by the general formula (134) and C is represented by the general formula (131).

5. The dye of claim 4, wherein $R_a$, $R_b$, $R_g$, and $R_h$ each represent $C_mH_{2m+1}$ (m=1 to 15) or $OC_pH_{2p+1}$ (p=1 to 15).

6. The dye of claim 5, wherein $R_a$, $R_b$, $R_g$, and $R_h$ each represent tert-butyl or —$C_6H_{13}$.

7. The dye of claim 1, wherein B, C, and D each are represented by the general formula (134).

8. The dye of claim 7, wherein $R_g$ and $R_h$ each represent $C_mH_{2m+1}$ (m=1 to 15) or $OC_pH_{2p+1}$ (p=1 to 15).

9. The dye of claim 8, wherein $R_g$ and $R_h$ each represent tert-butyl or —$C_6H_{13}$.

10. The dye of claim 1, wherein B, C, and D each are represented by the general formula (131).

11. The dye of claim 10, wherein $R_a$ and $R_b$ each represent $C_mH_{2m+1}$ (m=1 to 15) or $OC_pH_{2p+1}$ (p=1 to 15).

12. The dye of claim 11, wherein $R_a$ and $R_b$ each represent tert-butyl or —$C_6H_{13}$.

13. A dye for a dye-sensitized solar cell, wherein the dye is represented by the following general formula (200):

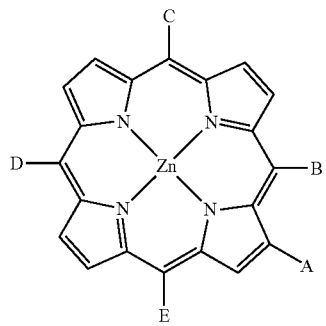

wherein A is represented by one of the following general formulae (111) to (118),

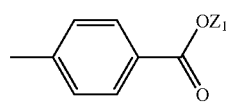

111

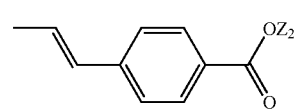

112

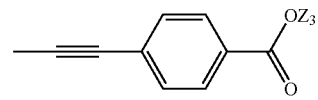

113

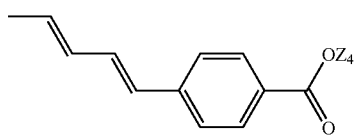

114

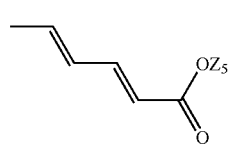

115

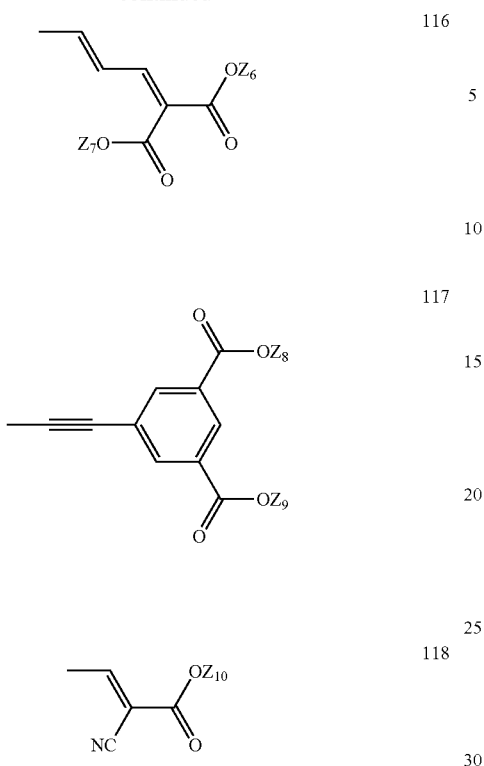
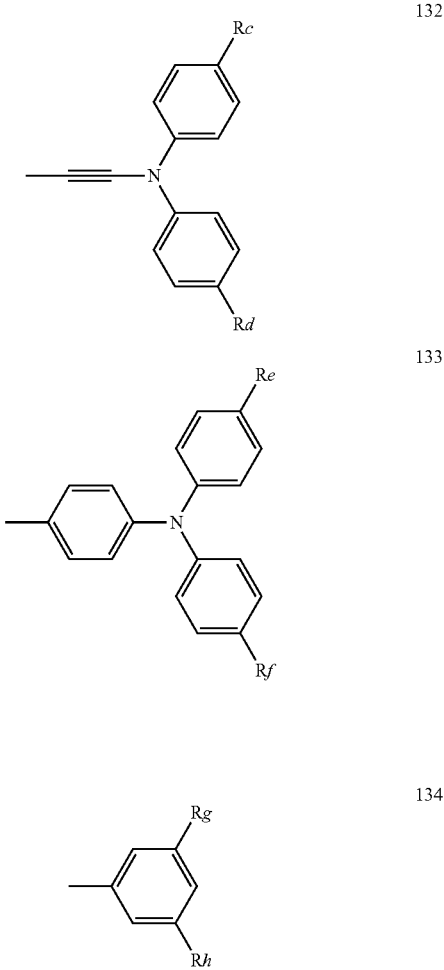
wherein $Z_1$ to $Z_{10}$ independently represent a hydrogen atom (H), lithium (Li), sodium (Na), or tetra-alkyl ammonium group represented by the following general formula (120),
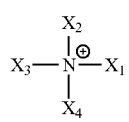
wherein $X_1$ to $X_4$ independently represent $C_mH_{2m+1}$ (m=1 to 6), and B, C, D, and E are the same or different, and independently represented by one of the following general formulae (131) to (140):
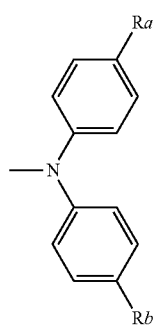
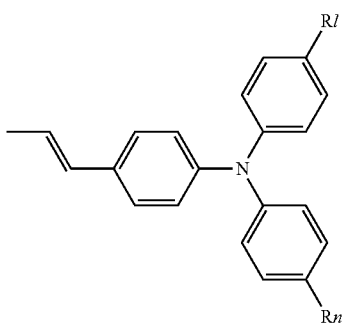

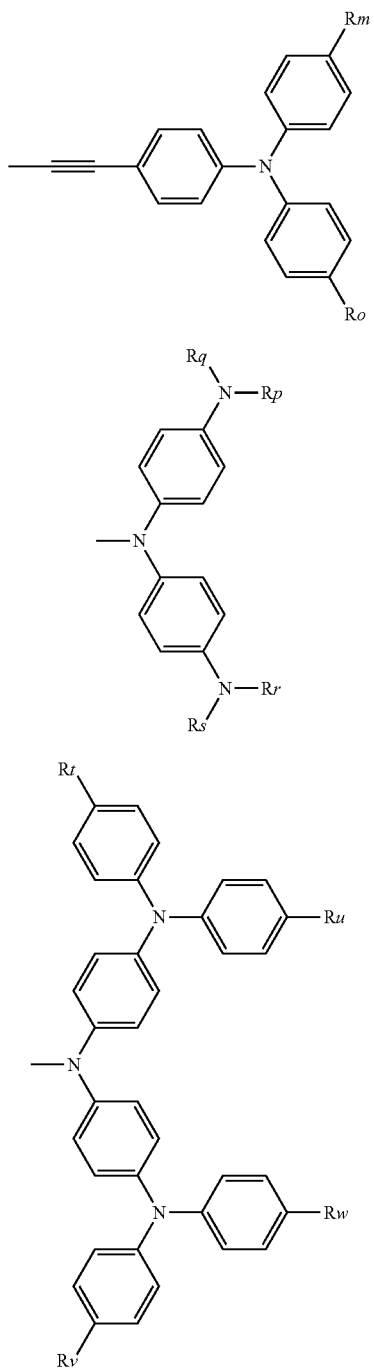

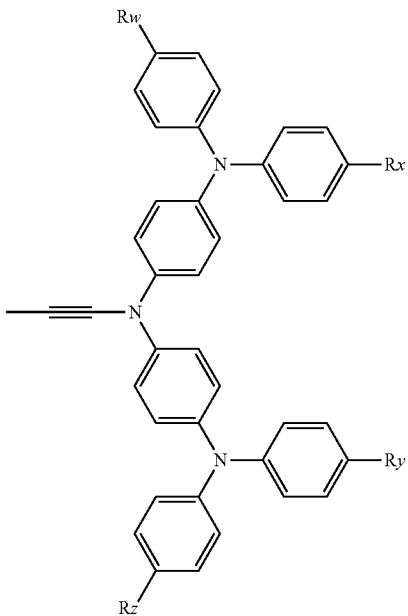

wherein $R_a$ to $R_z$ are independently selected from the group consisting of H, $C_mH_{2m+1}$ (m=1 to 15), $OC_pH_{2p+1}$ (p=1 to 15), $CH_2[OC_2H_4]_nOCH_3$ (n=1 to 30), and $[OC_2H_4]_qOCH_3$ (q=1 to 30).

14. The dye of claim 13, wherein A is represented by the general formula (113).

15. The dye of claim 14, wherein $Z_3$ represents a hydrogen atom (H).

16. The dye of claim 13, wherein B, C, and E each are represented by the general formula (134) and D is represented by the general formula (131).

17. The dye of claim 16, wherein $R_a$, $R_b$, $R_g$, and $R_h$ each represent $C_mH_{2m+1}$ (m=1 to 15) or $OC_pH_{2p+1}$ (p=1 to 15).

18. The dye of claim 17, wherein $R_a$, $R_b$, $R_g$, and $R_h$ each represent tert-butyl or —$C_6H_{13}$.

19. The dye of claim 13, wherein B, C, D and E each are represented by the general formula (134).

20. The dye of claim 19, wherein $R_g$ and $R_h$ represent $C_mH_{2m+1}$ (m=1 to 15) or $OC_pH_{2p+1}$ (p=1 to 15).

21. The dye of claim 20, wherein $R_g$ and $R_h$ each represent tert-butyl or —$C_6H_{13}$.

22. The dye of claim 13, wherein B, C, D, and E each are represented by the general formula (131).

23. The dye of claim 22, wherein $R_a$ and $R_b$ each represent $C_mH_{2m+1}$ (m=1 to 15) or $OC_pH_{2p+1}$ (p=1 to 15).

24. The dye of claim 23, wherein $R_a$ and $R_b$ each represent tert-butyl or —$C_6H_{13}$.

* * * * *